(12) United States Patent
Talish et al.

(10) Patent No.: US 7,942,835 B2
(45) Date of Patent: May 17, 2011

(54) SYSTEM AND METHOD FOR PROVIDING THERAPEUTIC TREATMENT USING A COMBINATION OF ULTRASOUND AND VIBRATIONAL STIMULATION

(75) Inventors: Roger J. Talish, Hillsborough, NJ (US); Clinton T. Rubin, Port Jefferson, NY (US); Kenneth J. McLeod, Vestal, NY (US)

(73) Assignee: American Medical Innovations, L.L.C., Fort Myers Beach, FL (US)

( * ) Notice: Subject to any disclaimer, the term of this patent is extended or adjusted under 35 U.S.C. 154(b) by 442 days.

(21) Appl. No.: 11/716,075

(22) Filed: Mar. 8, 2007

(65) Prior Publication Data
US 2007/0232963 A1     Oct. 4, 2007

Related U.S. Application Data

(60) Provisional application No. 60/873,327, filed on Dec. 7, 2006, provisional application No. 60/780,336, filed on Mar. 8, 2006.

(51) Int. Cl.
*A61N 7/00* (2006.01)
(52) U.S. Cl. .......................................................... 601/2
(58) Field of Classification Search ....................... 601/2
See application file for complete search history.

(56) References Cited

U.S. PATENT DOCUMENTS

| | | |
|---|---|---|
| 4,013,069 A | 3/1977 | Hasty |
| 4,530,360 A | 7/1985 | Duarte |
| 4,858,599 A | 8/1989 | Halpern |
| 5,003,965 A | 4/1991 | Talish et al. |
| 5,046,484 A | 9/1991 | Bassett et al. |
| 5,103,806 A | 4/1992 | McLeod et al. |
| 5,145,027 A | 9/1992 | Petzl et al. |
| 5,186,162 A | 2/1993 | Talish et al. |
| 5,191,880 A * | 3/1993 | McLeod et al. ................ 601/2 |
| 5,211,160 A | 5/1993 | Talish et al. |
| 5,273,028 A | 12/1993 | McLeod et al. |

(Continued)

FOREIGN PATENT DOCUMENTS

EP            0 029 298 A1      5/1981

(Continued)

OTHER PUBLICATIONS

PCT Notification of Transmittal of The Internationa Search Report and The Written Opinion of the International Searching Authorityfor International Appln. No. PCT/US2007/005792, dated Sep. 12, 2007.

(Continued)

*Primary Examiner* — Eric F Winakur
*Assistant Examiner* — Hien Nguyen
(74) *Attorney, Agent, or Firm* — Malloy & Malloy, P.A.

(57) ABSTRACT

A system and method are disclosed for providing therapeutic treatment using a combination of ultrasound and vibrational stimulation. The system includes a first therapeutic treatment system or Dynamic Motion Therapy system having a vibrational assembly having a non-rigidly supported platform for generating resonant vibrations. The system further includes a second therapeutic treatment system configured to operate either alone or in conjunction with the first therapeutic treatment system. The second therapeutic treatment system includes an ultrasound transducer assembly which generates ultrasonic waves. In one embodiment, the ultrasonic waves are modulated by the resonant vibrations. One method includes: a) applying vibrational stimulation to a patient's body; and b) simultaneously or non-simultaneously applying an ultrasonic stimulation to the patient's body during a treatment session.

2 Claims, 4 Drawing Sheets

U.S. PATENT DOCUMENTS

| | | | |
|---|---|---|---|
| 5,376,065 A | 12/1994 | McLeod et al. | |
| 5,437,668 A | 8/1995 | Aronson et al. | |
| 5,520,612 A | 5/1996 | Winder et al. | |
| 5,538,489 A | 7/1996 | Magid | |
| 5,556,372 A | 9/1996 | Talish et al. | |
| 5,730,705 A | 3/1998 | Talish et al. | |
| 5,762,616 A | 6/1998 | Talish | |
| 5,904,604 A * | 5/1999 | Suzuki et al. | 440/84 |
| 5,904,659 A * | 5/1999 | Duarte et al. | 601/2 |
| 5,971,984 A | 10/1999 | Taylor et al. | |
| 5,997,490 A | 12/1999 | McLeod et al. | |
| 6,050,364 A | 4/2000 | Popall et al. | |
| 6,234,975 B1 | 5/2001 | McLeod et al. | |
| 6,440,046 B1 | 8/2002 | Tholkes | |
| 6,558,304 B1 | 5/2003 | Bardon et al. | |
| 6,561,991 B2 | 5/2003 | McLeod et al. | |
| 6,607,497 B2 | 8/2003 | McLeod et al. | |
| 6,610,021 B1 | 8/2003 | Bock | |
| 6,620,117 B1 | 9/2003 | Johnson et al. | |
| 6,843,776 B2 | 1/2005 | Trandafir et al. | |
| 6,884,227 B2 | 4/2005 | Krompasick | |
| 6,902,320 B2 | 6/2005 | McKenna | |
| 2004/0059331 A1 | 3/2004 | Mullaney | |
| 2004/0260211 A1 | 12/2004 | Maalouf | |
| 2005/0193820 A1 * | 9/2005 | Sheljaskow et al. | 73/649 |
| 2006/0047230 A1 * | 3/2006 | Talish | 601/46 |
| 2006/0200054 A1 | 9/2006 | Talish et al. | |
| 2006/0217640 A1 | 9/2006 | Trandafir | |
| 2006/0241528 A1 | 10/2006 | Talish | |
| 2007/0038165 A1 | 2/2007 | Trandafir et al. | |
| 2007/0055185 A1 | 3/2007 | Trandafir et al. | |

FOREIGN PATENT DOCUMENTS

| | | |
|---|---|---|
| EP | 1 656 921 A1 | 5/2006 |
| WO | WO95/21580 | 8/1995 |
| WO | WO 02/053084 A1 | 7/2002 |
| WO | WO 2006/096662 A1 | 9/2006 |
| WO | WO 2006/096734 A1 | 9/2006 |

OTHER PUBLICATIONS

Walsh, W.R. et al,, Influence of Dynamic Motion Therapy on bone ingrowth into a bone graft substitute, Surg. & Ortho. Research Labs., Univ. of New S. Wales, Australia.

PCT Notification of Transmittal of The International Search Report and The Written Opinion of the International Searching Authority for PCT/US2007/005794,dated Aug. 30,2007.

* cited by examiner

SYSTEM AND METHOD FOR PROVIDING THERAPEUTIC TREATMENT USING A COMBINATION OF ULTRASOUND AND VIBRATIONAL STIMULATION

PRIORITY

The present application claims priority from U.S. Provisional Application Ser. No. 60/873,327, entitled "Non-Invasive Apparatuses And Methods For Vibrational Treatment Of Bone Tissue Following A Bone-Related Medical Procedure," filed on Dec. 7, 2006. The present application also claims priority from U.S. Provisional Application Ser. No. 60/780,336, entitled "System and Method for Providing Therapeutic Treatment Using a Combination of Ultrasound, Electro-Stimulation and Dynamic Motion Therapy," filed on Mar. 8, 2006. The entire contents of both applications are incorporated herein by reference.

CROSS-REFERENCE TO RELATED APPLICATIONS

This application is related to United States and PCT patent applications filed on Mar. 8, 2007 and both entitled "System and Method for Providing Therapeutic Treatment Using a Combination of Ultrasound, Electro-stimulation and Vibrational Stimulation" by Talish et al. The entire contents of these applications are incorporated herein by reference.

BACKGROUND

1. Technical Field

The present disclosure relates generally to therapeutic treatment. In particular, the present disclosure relates to a system and method using a combination of ultrasound and vibrational stimulation for providing therapeutic treatment.

2. Description of the Prior Art

Weakened bone structure and improperly healed or slowly healing bone fractures may result in reduced quality of life. Quality of life may be improved for patients with bone fractures by ensuring rapid healing and by inhibiting the loss of bone mineral content (bone mass), and therefore bone strength, associated with fractures. Metabolic bone diseases, such as osteoporosis, also reduce the quality of life.

Osteoporosis is a pernicious disorder usually, but not exclusively, afflicting elderly women. The osteoporotic state can also be manifested by those who are confined to bed and even to astronauts who are subjected to prolonged weightlessness. Osteoporosis occurs through a decrease in bone mass, which makes the afflicted bones more fragile and more susceptible to breakage.

The reduction in bone mass from osteoporosis results when destruction outpaces bone formation. The balance between destruction and formation is affected by hormones, calcium intake, vitamin D and its metabolites, weight, smoking, alcohol consumption, age, genetic determinants and especially exercise or other methods of dynamically loading the bone tissue as well as many other factors. Considering the vast array of factors which can compromise the healing process, any form of stimulation that can accelerate, augment and/or ensure the healing process are greatly needed.

Osteoporosis is not easily determined in its early phases as physical deformity is not yet evident. Because osteoporosis develops progressively, early diagnosis and appropriate treatment may avoid a serious condition. Appropriate diet and exercise can be used in early years to prevent the damaging effects of osteoporosis later in life.

Besides the nutritional and genetic causes of osteoporosis, bone loss also occurs from prolonged exposure to weightless environments, i.e., prolonged periods in space as experienced by the crews of the International Space Station. When these crews return to the normal gravity of Earth, their bone loss could make them more susceptible to fractures. The longer the duration of weightlessness experienced by an astronaut, the greater the resultant muscle and bone loss and, consequently, the greater the risk of injury or immobilization. Various techniques have been employed to minimize the impact of prolonged weightlessness with varying degrees of success.

Methods and apparatus for maintaining or promoting bone growth are described in numerous patents. For example, McLeod et al., U.S. Pat. Nos. 5,103,806, 5,191,880, 5,273,028, 5,376,065, 6,234,975, 6,561,991 B2 and 6,607,497 B2 all incorporated herein by reference, collectively describe means and methods for promoting bone growth and preventing bone loss. The method described in the above-referenced patents relates to a mechanical vibrational loading of bones to promote growth in a non-invasive procedure.

Mechanical loading on bone tissue at strains of between about 0.1 to about 500 microstrain and induced within a predetermined frequency range can prevent bone loss and enhance new bone formation. Such mechanical bone loading of tissue may be introduced by various systems, including vibrating floor plates and chairs such as ones used for the generation of resonant vibrations, electrical stimulation of muscles, isometric exercises, modulated ultrasound or transducers attached to the skin or external fixation devices to focus energy to the fracture site.

A method of using resonant vibrations for treating postural instability is described in U.S. Pat. No. 6,607,497 B2. The method includes the steps of (a) providing a vibration table having a non-rigidly supported platform; (b) permitting the patient to rest on the non-rigidly supported platform for a predetermined period of time; and (c) repeating the steps (a) and (b) over a predetermined treatment duration. Step (b) includes the steps of (b1) measuring a vibrational response of the patient's musculoskeletal system using a vibration measurement device; (b2) performing a frequency decomposition of the vibrational response to quantify the vibrational response into specific vibrational spectra; and (b3) analyzing the vibrational spectra to evaluate at least postural stability.

The method described in U.S. Pat. No. 6,607,497 B2 entails the patient standing on the vibration table or unstable standing platform, which includes at least one accelerometer mounted to the outboard side thereof. The patient is then exposed to a vibrational stimulus by the unstable standing platform. The unstable standing platform causes a vibrational perturbation of the patient's neurosensory control system. The vibrational perturbation causes signals to be generated within at least one of the patient's muscles to create a measurable response from the musculoskeletal system. These steps are repeated over the course of a predetermined treatment duration for approximately ten minutes a day in an effort to improve the postural stability of the patient.

The therapeutic benefits of ultrasound have also long been known. Ultrasound therapy uses high-energy sound waves (those above the range we hear) to help ease painful joints and muscles. Ultrasound treatment is generally performed by an operator who guides the waves into the body from the head of an ultrasound machine. Examples, as seen in Duarte, U.S. Pat. No. 4,530,360, and Talish et al., U.S. Pat. Nos. 5,556,372, 5,762,616, and 5,730,705, all incorporated herein by reference, collectively describe means and methods of implementing ultrasound for treating injuries. In Duarte, in order to apply the ultrasound pulses during treatment, the operator manually holds the applicator in place until treatment is complete. The longer the treatment period, the more the patient is inconvenienced. Talish overcame the shortcomings of Duarte by combining the ultrasound apparatus with a harness. Thus, Talish, bestows the operator with a degree of freedom that is not evident in Duarte. For example, Talish, because of the harness, allows a user to receive treatment while performing everyday activities.

SUMMARY

The present disclosure provides a system and method for providing therapeutic treatment using a combination of ultrasound and vibrational (Dynamic Motion Therapy) stimulation. The combined therapeutic system includes a combination of at least two therapeutic systems for providing the therapeutic treatment. The system includes a first therapeutic treatment system or Dynamic Motion Therapy system that includes a supporting base and a vibrational assembly having a non-rigidly supported platform for generating resonant vibrations. Additionally, the system includes a second therapeutic treatment system configured to operate either alone or in conjunction with the first therapeutic treatment system. The second therapeutic system is an ultrasound treatment system having an ultrasound transducer assembly for generating ultrasonic waves. The resonant vibrations cause the vibrational stimulation and the ultrasonic waves cause the ultrasound stimulation.

The system further includes a controller in electrical communication with the therapeutic treatment systems. The controller provides operational signals for operating the therapeutic treatment systems.

A method according to the present disclosure includes: a) applying vibrational stimulation to a patient's body; and b) simultaneously or non-simultaneously applying ultrasound stimulation to the patient's body during a treatment session.

The ultrasound transducer assembly can include an ultrasound transducer and a motion sensor. In one embodiment, the motion sensor can be a gravitational switch. In another embodiment, the motion sensor can be an accelerometer. The motion sensor, in one embodiment, can be powered by the first therapeutic treatment system, and in another embodiment, the motion sensor can have its own power source, such as a battery.

The ultrasound transducer assembly of the second therapeutic treatment system can be automatically activated and deactivated by the first therapeutic treatment system. The ultrasound transducer assembly is activated when the motion sensor detects motion created by the first therapeutic treatment system applying resonant vibrations to the patient's body causing the patient to sway or move, and the ultrasound transducer assembly is deactivated when the first therapeutic treatment system is turned off and the patient stops swaying or moving.

DETAILED DESCRIPTION

Detailed embodiments of the present disclosure are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Some of the therapeutic benefits of Dynamic Motion Therapy are that it prevents and reverses the loss of muscle and bone tissue (these are two characteristics of osteoporosis), it reduces the possibility of spinal or hip fractures, it is an excellent option for those unable or unwilling to take osteoporosis medication, it is noninvasive and less costly than chronic drug therapy, it is gentle in its repetitive vertical movement, it is convenient with a daily treatment of less than 1 hour and preferably about 10 to 20 minutes, and it is simple, mobile and safe to use.

Furthermore, because the present disclosure incorporates the known beneficial effects of ultrasound therapy with Dynamic Motion Therapy, therapeutic benefits, not found when either system is used separately, can be attained. The combination of vibrational and ultrasound stimulation can massage soft tissues effortlessly, and in most cases, painlessly. In addition, the system and method in accordance with the present disclosure help alleviate muscle spasms and reduce inflammation and swelling. Also, the system and method in accordance with the present disclosure improve range of motion, help increase blood flow and interstitial fluid flow, promote bone growth, and decrease pain and stiffness.

Figure 1:
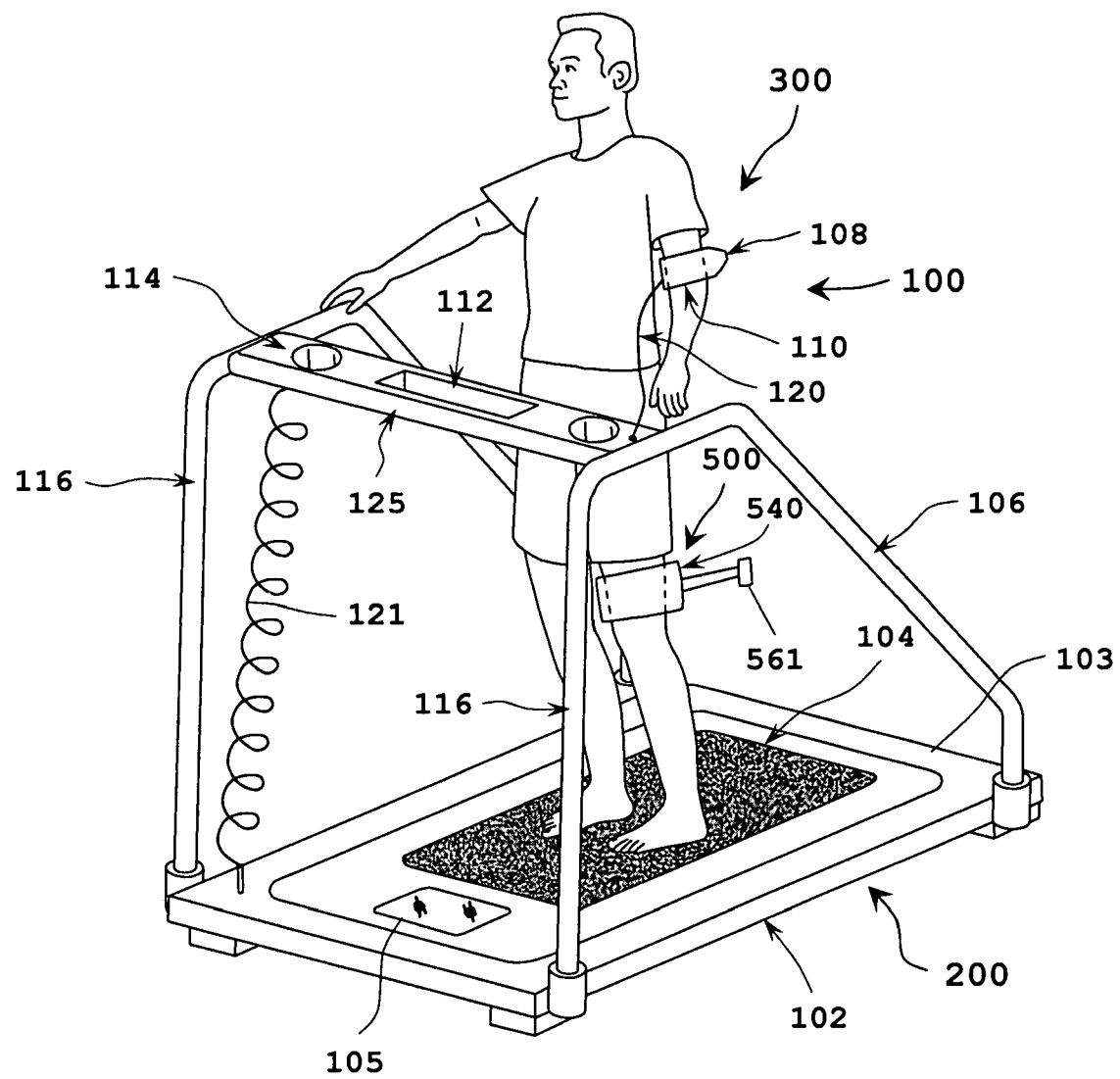
FIG. 1 is a perspective view of a system for providing combined vibrational and ultrasound stimulation in accordance with the present disclosure.

Referring to FIG. 1, the present disclosure provides a combined ultrasound and vibrational treatment (UVT) system 100 for providing therapeutic treatment using a combination of ultrasound and vibrational stimulation. The UVT system 100 incorporates a first therapeutic treatment system or Dynamic Motion Therapy system 200 having a vibrational assembly 102. The UVT system 100 further includes a second therapeutic treatment system 300 having an ultrasound transducer assembly 110; both assemblies 102, 110 are controlled by receiving signals from a controller 112. The controller 112 includes a power supply for powering the assemblies 102, 110. Alternatively, each assembly is controlled by its own controller and/or power supply.

A vibrational assembly that can be implemented with the present disclosure can be the assembly described in International Patent Application WO 2006/096734 A1, Talish et al., filed on Mar. 7, 2006, the contents of which are hereby incorporated by reference. Another type of vibrational assembly that can be implemented with the present disclosure can be the assembly described in International Patent Application WO 2006/096662 A1, also by Talish et al., filed on Mar. 6, 2006, the contents of which are hereby incorporated by reference.

With continued reference to FIG. 1, an exemplary vibrational assembly 102 of the present disclosure includes a base 103 dimensioned to support and comfortably accommodate a patient in a standing position. The base 103 non-rigidly supports a vibrational platform 104 of the vibrational assembly 102, configured to impart or apply resonant vibrations to the musculoskeletal system of a patient's body. The vibrational assembly 102 generates resonant vibrations (Step 1 in FIG. 2) having a frequency in the range of between 1 to 10 kHz. The resonant vibrations cause a vibrational stimulation. The vibrational stimulation is applied to the patient being supported by the platform 104 (Step 2 of FIG. 2).

For patient stability and comfort, handrails 106 are provided; allowing the patient to easily remain in a proper posture and maintain balance while the vibration treatment is being administered. Additionally, a standing harness may be provided, aiding patients unable to stand on their own to maintain proper posture. The vibrational assembly 102 further includes a display 105 for displaying data, such as treatment data.

As mentioned above, the UVT system 100 also includes a second therapeutic treatment system 300 that has the ultrasound transducer assembly 110 for facilitating bone fracture healing and/or bone/soft tissue treatment, such as treating joint and muscle sprains, bursitis, tendonitis, and the like. The UVT system 100 can include numerous types of ultrasound transducer assemblies. Some, for example, can include those as disclosed in the patents listed above and issued to Duarte and Talish et al.

The ultrasound transducer assembly 110 during treatment is actuated to generate ultrasonic waves. The ultrasonic waves cause ultrasound stimulation. The ultrasound stimulation is applied to the patient supported by the platform (Step 3 of FIG. 2). The controller 112 controls the operational parameters of the UVT system 100 based on received signals from sensors positioned on the patient and/or within the ultrasound transducer assembly 110 (Step 4 of FIG. 2). By controlling the operational parameters, such as amplitude and frequency of the resonant vibrations and/or ultrasonic waves, the level or intensity of the vibrational and/or ultrasonic stimulations is changed.

Figure 2:
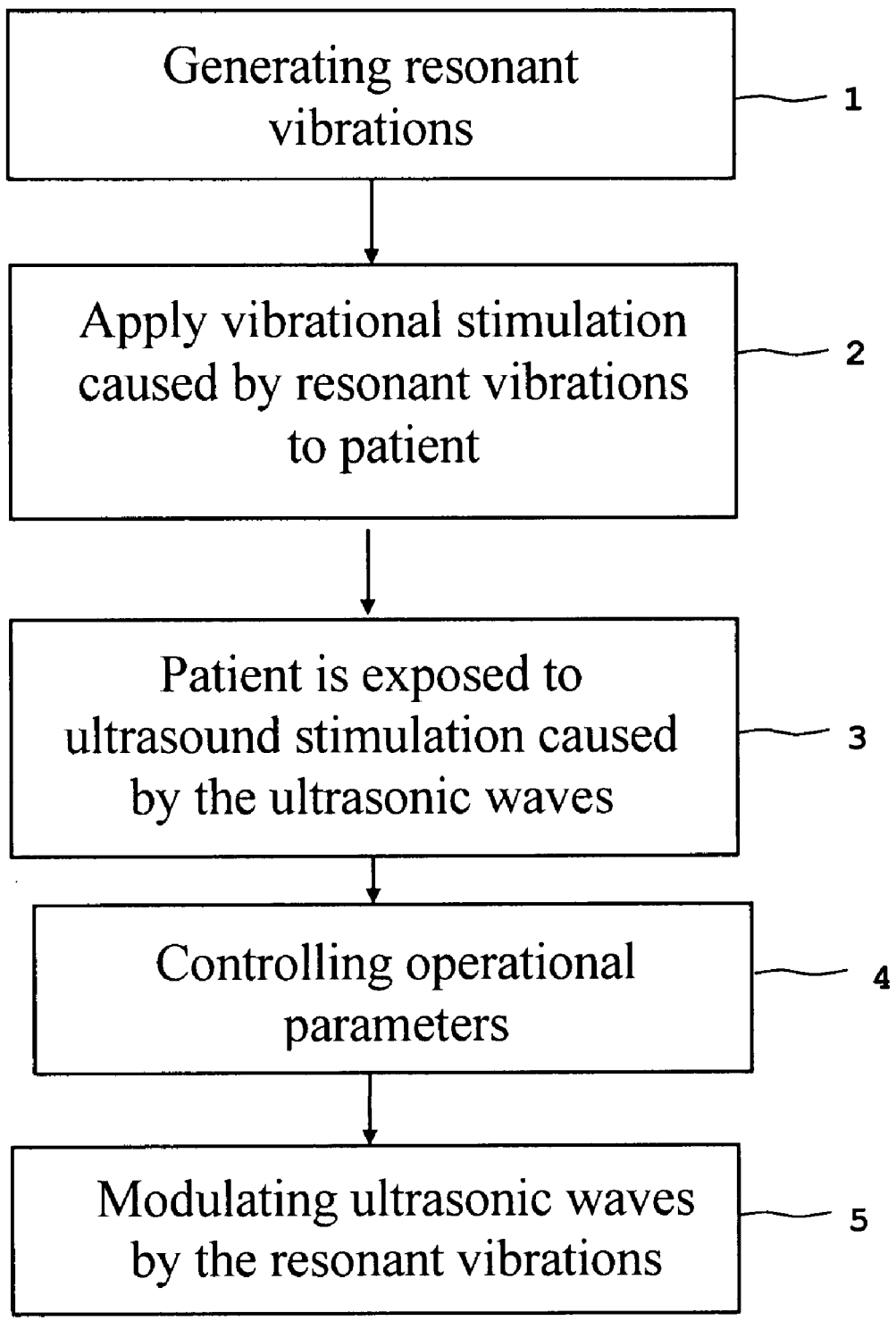
FIG. 2 is a flow chart illustrating an exemplary method for providing combined vibrational and ultrasound stimulation in accordance with the present disclosure.

One of the key features of the present disclosure is that the resonant vibrations generated by the vibrational assembly 102 modulate the continuous ultrasonic waves generated by the ultrasound transducer assembly 110 (Step 5 of FIG. 2). For example, during treatment, the ultrasound transducer assembly 110 is placed on a patient, such that the transducer head of the assembly 110 is positioned in proximity to a bone breakage, such as a hairline fracture (e.g., less than a mm wide). Upon actuation of the ultrasound transducer assembly 110, an ultrasound signal (carrier signal) is generated having a frequency in the range of 1-3 MHz, for example, a frequency of 1.5 MHz, and directed by the transducer head towards the hairline fracture. If the patient is standing on the vibrational platform 104 of the vibrational assembly 102 which has been actuated to generate resonant vibrations having a frequency in the range of 1-10 kHz, the bone having the hairline fracture or breakage vibrates at the same frequency as the resonant vibrations. This causes the ultrasound signal or waves within the hairline fracture to be modulated, thereby producing or setting up a modulated shear wave within the hairline fracture due to the cavitation effect. The shear wave can be a standing wave which facilitates the stimulation of bone tissue growth, thereby effectively accelerating the healing of the hairline fracture.

The above-referenced embodiments, as hereinbefore disclosed, provide for using an ultrasound transducer assembly 110 which generates ultrasonic waves having frequencies in the range of 1-3 MHz. It is envisioned that the ultrasound transducer assembly 110 can generate ultrasonic waves having low frequencies, that is, 20-100 kHz. If the ultrasound transducer assembly of the present disclosure, is operated to generate ultrasonic waves having low frequencies, it can be used for wound debridement and bacterial removal, which further promote wound and bone fracture healing.

Figure 3:
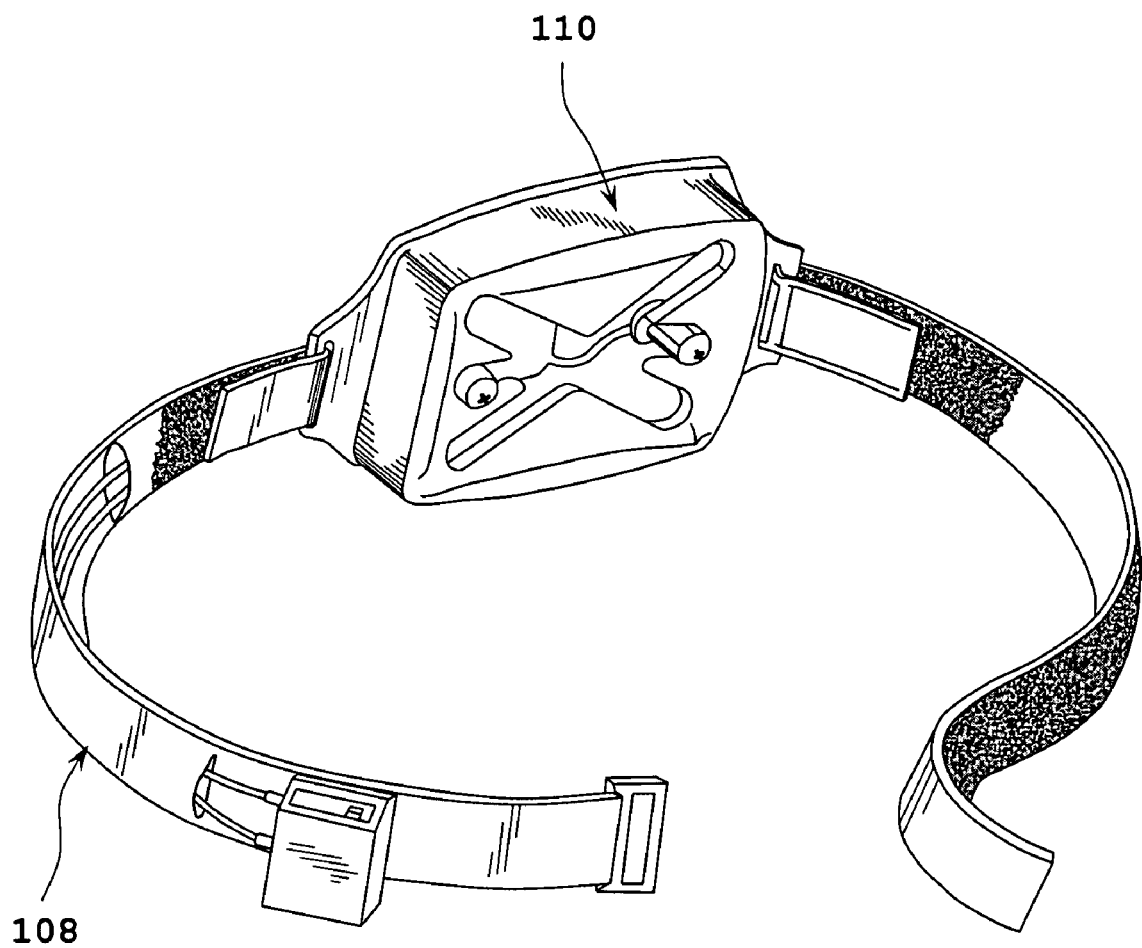
FIG. 3 is a perspective view of an ultrasound transducer assembly in accordance with the present disclosure.

With reference to FIG. 3, one embodiment of the ultrasound transducer assembly 110 is equipped with a cuff 108 capable of being fastened to the patient's body, e.g., leg, arm. The cuff 108 contains an embedded ultrasound transducer (not shown) for delivering ultrasound energy to the treatment area. Multiple ultrasound transducers may be embedded within the cuff 108 to provide multiple ultrasound energy radiating from a plurality of positions and angles. Each ultrasound transducer may be individually controllable by the controller 112. Additional cuffs 108 may be made available to allow for treatment of multiple locations, such that, for example, both legs, and the thigh and calf areas of the same leg may be treated at the same time.

The therapeutic treatment systems are, preferably, individually controllable such that a variety of treatment regimens may be devised. Additionally, a course of treatment may require alternating between the two therapeutic treatment systems for periods of time throughout the duration of a treatment session. For example, the vibrational assembly 102 may be operated for the full treatment session while the ultrasound transducer assembly 110 is operated for 10-second periods during the treatment session. As a second example, the vibrational assembly 102 is operated for 20 minutes followed by operation of the ultrasound transducer assembly 110 for 30 minutes. These are just two examples of the endless variations of timing sequences that are possible using the UVT system 100 of the present disclosure. The treatment session can be at least 10 minutes per day. The duration of the treatment can be 2-4 weeks.

As mentioned above, the first and second therapeutic treatment systems are controlled via the controller 112. In a preferred embodiment, controller 112 can be housed in front member 114. Member 114 can be of any suitable shape known in the available art. In addition, member 114 can have a plethora of different features. For example, member 114 can have a diagnostic panel that displays different operating parameters of the ultrasound transducer assembly 110. Also, member 114 can have another diagnostic panel that displays different operating parameters of assembly 102. Member 114 can also be equipped with heart-rate displays, pulse-rate displays, calorie counter displays, fans and the like. These features can be added or removed as needed. Furthermore, located on member 114 can be control switches, buttons and the like used for controlling both the ultrasound transducer assembly 110 and the vibrational assembly 102. Controller 112 can be connected to the ultrasound transducer assembly 110 via a cable 120, as seen in FIG. 1.

In an alternative embodiment, controller 112 can control ultrasound transducer assembly 110 remotely. If the embodiment that utilizes a cable is used, the cable can be threaded through either of support bars 116. Or, in an alternative embodiment, as seen in FIG. 1, a cable 121 can be used. In this embodiment, cable 121 can extend from a bottom surface 125 of member 114 to the top surface 104. The cable connections described are for illustrative purposes only, and by no means should be considered exhaustive of the many different connections available. Therefore, any suitable connection means known in the available art, or those connection means not yet discovered can be implemented with the present disclosure.

Other treatment scenarios include having one or both assemblies (vibrational and ultrasound assemblies 102 and 110) operational or active during at least a portion of the treatment session, but at least one of the assemblies' operating parameters are adjusted manually or automatically during the treatment session or a portion thereof. The operating parameters can be adjusted independently of the other assemblies' operating parameters, or adjusted dependently, i.e., in accordance with, with changes in the operating parameter(s) of the other system. Additionally, the assemblies of the present disclosure can be designed wherein an operating parameter of the first therapeutic treatment system changes in accordance with a change in an operating parameter of the second therapeutic treatment system. For example, during the treatment duration, the frequency of the vibrational assembly 102 can be increased by 5 Hz for each increase in the power output of the ultrasound transducer assembly 110 of more than a predetermined wattage value. Therefore, an increase in the frequency of the vibrational assembly 102 depends on an increase in the power output of the ultrasound transducer assembly 110.

The present disclosure also includes a method for providing a combined therapeutic treatment using the two different therapeutic treatment systems. The method includes: a) applying vibrational stimulation to a patient's body; and b) simultaneously or non-simultaneously applying ultrasonic stimulation to the patient's body during a treatment session.

Figure 4:
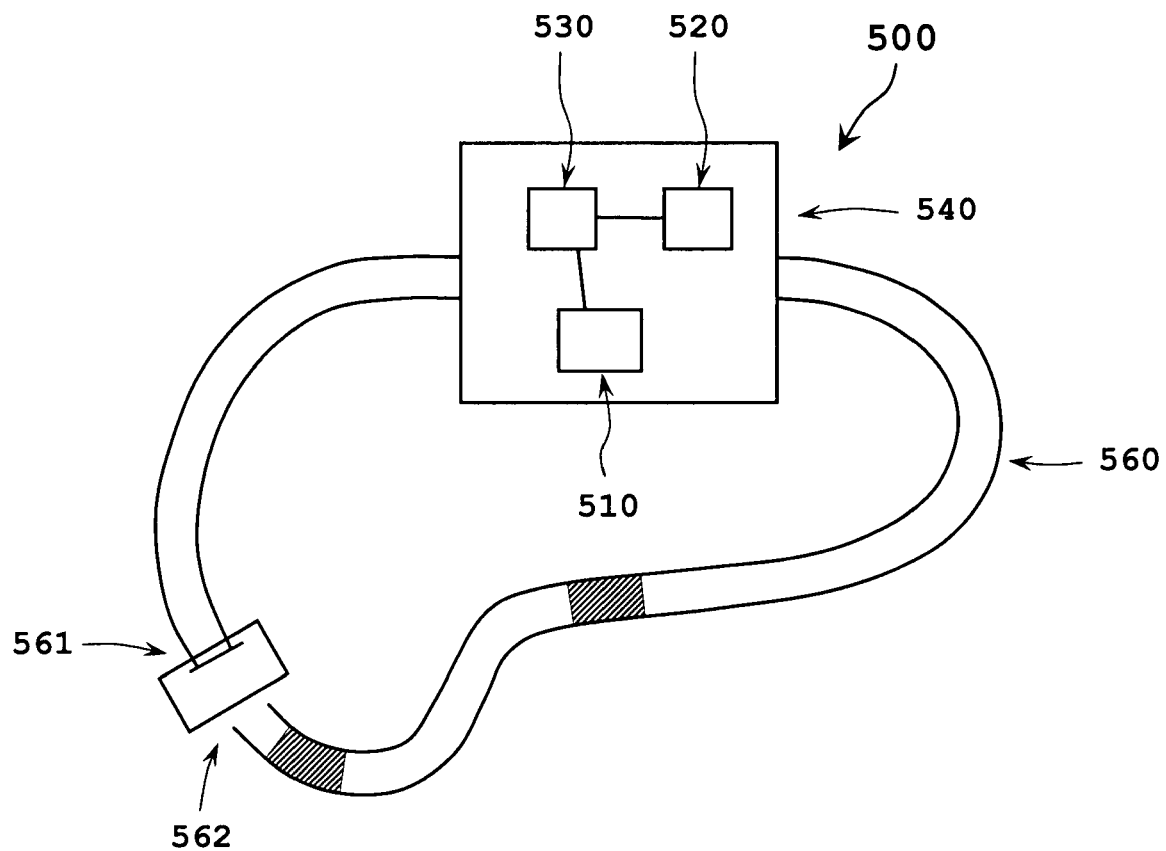
FIG. 4 is an alternative, partial perspective view of an ultrasound transducer assembly in accordance with the present disclosure.

With reference to FIG. 4, there is shown an alternative embodiment for an ultrasound transducer assembly in accordance with the present disclosure. The assembly 500 includes an ultrasound transducer 510, a power source 520, and an actuation controller 530. These components are housed within a housing 540. The actuation controller 130 is a motion sensor, such as a gravity switch or an accelerometer. The assembly 500 further includes a strap 560 having a first end 561 and a second end 562 capable of connecting to each other for strapping the assembly 500 to a patient.

The described embodiments of the present disclosure are intended to be illustrative rather than restrictive, and are not intended to represent every embodiment of the present disclosure. Various modifications and variations can be made without departing from the spirit or scope of the present disclosure as set forth in the following claims both literally and in equivalents recognized in law.

What is claimed is:

1. A system having at least two therapeutic systems for providing therapeutic treatment to a patient, said system comprising:
    a first therapeutic treatment system comprising a non-rigidly supported platform configured to support the patient, said platform configured to generate vibrations and to impart said generated vibrations to the patient,
    a second therapeutic treatment system configured to operate either alone or in conjunction with said first therapeutic treatment system during a treatment session, said second therapeutic treatment system configured to generate ultrasonic waves,
    wherein said ultrasonic waves generated by said second therapeutic treatment system are modulated by said generated vibrations, and
    a controller configured to automatically change an operating parameter of said first therapeutic treatment system in accordance with a change in an operating parameter of said second therapeutic treatment system, wherein said operating parameter of said first therapeutic treatment system is a frequency of vibration of said platform, and said controller is configured to increase said frequency of vibration of said platform when said operating parameter of said second therapeutic system increases by more than a predetermined value.

2. The system of claim 1, wherein said operating parameter of said second therapeutic system is a power output of said second therapeutic system.

* * * * *